United States Patent
Ormsby et al.

(10) Patent No.: US 7,070,595 B2
(45) Date of Patent: Jul. 4, 2006

(54) RADIO-FREQUENCY BASED CATHETER SYSTEM AND METHOD FOR ABLATING BIOLOGICAL TISSUES

(75) Inventors: Theodore C. Ormsby, Milpitas, CA (US); Ming-Fan Law, San Diego, CA (US); George L. Leung, San Diego, CA (US)

(73) Assignee: Medwaves, Inc., San Diego, CA (US)

( * ) Notice: Subject to any disclaimer, the term of this patent is extended or adjusted under 35 U.S.C. 154(b) by 345 days.

(21) Appl. No.: 10/637,325

(22) Filed: Aug. 8, 2003

(65) Prior Publication Data
US 2004/0106917 A1  Jun. 3, 2004

Related U.S. Application Data

(63) Continuation-in-part of application No. 10/306,757, filed on Nov. 27, 2002, now Pat. No. 7,004,938, which is a continuation-in-part of application No. 09/459,058, filed on Dec. 11, 1999, now Pat. No. 6,663,625, which is a continuation-in-part of application No. 09/211,188, filed on Dec. 14, 1998, now Pat. No. 6,190,382.

(51) Int. Cl.
A61B 18/04 (2006.01)

(52) U.S. Cl. .................. 606/33; 607/101; 607/152; 607/154

(58) Field of Classification Search ............... 606/41, 606/32, 47, 129, 50, 34, 4; 607/96, 101, 607/115, 116, 152, 154, 156; 128/898
See application file for complete search history.

(56) References Cited

U.S. PATENT DOCUMENTS

| | | | |
|---|---|---|---|
| 2,847,990 A | 9/1958 | Ayre | |
| 3,058,473 A | 10/1962 | Whitehead | |
| 3,521,620 A | 7/1970 | Cook | |
| 3,552,384 A | 1/1971 | Pierie et al. | |
| 4,723,936 A | 2/1988 | Buchbinder et al. | |
| 4,776,086 A | 10/1988 | Kasevich et al. | |
| 4,906,230 A | 3/1990 | Maloney et al. | |
| 4,960,134 A | 10/1990 | Webster, Jr. | |
| 5,843,076 A | 12/1998 | Webster, Jr. et al. | |
| 5,857,997 A | 1/1999 | Cimino et al. | |
| 5,863,291 A | 1/1999 | Schaer | |
| 5,876,373 A | 3/1999 | Giba et al. | |
| 5,882,333 A | 3/1999 | Schaer et al. | |
| 5,897,529 A | 4/1999 | Ponzi | |
| 5,904,667 A | 5/1999 | Falwell | |
| 5,916,241 A * | 6/1999 | Rudie et al. ................ 607/101 |

(Continued)

*Primary Examiner*—Rosiland Rollins
(74) *Attorney, Agent, or Firm*—Stephen C. Beuerle; Procopio Cory Hargreaves & Savitch LLP

(57) ABSTRACT

A method for biological tissue ablation includes shaping a shapeable RF antenna to accommodate the contour of a body vessel adjacent a biological tissue load; generating a train of radio frequency (RF) energy pulses at an output frequency for transmission in a transmission line to the shapeable RF antenna adjacent the biological tissue load; sensing a reflected signal and a forward signal of the RF energy pulses; and adjusting output frequency of the RF energy pulses to effect a substantial match of transmission line impedance with shapeable RF antenna and biological tissue load impedance.

28 Claims, 4 Drawing Sheets

U.S. PATENT DOCUMENTS

| | | |
|---|---|---|
| 6,029,051 A * | 2/2000 | Osterberg et al. ........ 455/115.1 |
| 6,071,280 A | 6/2000 | Edwards et al. |
| 6,183,463 B1 | 2/2001 | Webster, Jr. |
| 6,254,568 B1 | 7/2001 | Ponzi |
| 6,267,746 B1 | 7/2001 | Bumbalough |
| 6,356,790 B1 | 3/2002 | Maguire et al. |
| 6,383,182 B1 | 5/2002 | Berube et al. |
| 6,500,167 B1 | 12/2002 | Webster, Jr. |

* cited by examiner

RADIO-FREQUENCY BASED CATHETER SYSTEM AND METHOD FOR ABLATING BIOLOGICAL TISSUES

RELATED APPLICATIONS

This application is a continuation-in-part of U.S. patent application Ser. No. 10/306,757, filed Nov. 27, 2002 now U.S. Pat. No. 7,004,938, which is a continuation-in-part of U.S. patent application Ser. No. 09/459,058, filed Dec. 11, 1999 now U.S. Pat. No. 6,663,625, which is continuation-in-part of U.S. patent application Ser. No. 09/211,188 filed Dec. 14, 1998, now U.S. Pat. No. 6,190,382.

FIELD OF THE INVENTION

The present invention concerns a Radio Frequency (RF) based catheter system for ablating tissue and occlusions, particularly within liquid-filled lumens of animals, such as heart, liver, arteries and vessels of a human, with an electrical field produced about an RF antenna. More particularly, the invention concerns an apparatus providing an impedance match between an electrosurgical electrode, such as an antenna, and its environs, by controllably adjusting the frequency to minimize RF energy reflection.

BACKGROUND

This invention relates generally to radio frequency ("RF") powered medical apparatus and ablation of biological tissues. More particularly, this invention concerns RF generators for synthesizing and controlling RF energy over a range of microwave frequency to efficiently communicate with catheter-based RF antenna for ablating biological tissues within the body vessel of a patient and for the treatment of cardiac arrhythmia, solid tumor, etc.

In recent years medical devices have gained significant acceptance in the medical community as an important treatment modality for heart diseases and other serious ailments, which were traditionally remedied by medication or surgical operation. Two fundamental trends have emerged in the treatment of cardiac diseases. The first has been the shift from open-heart surgical procedures to less invasive and less expensive catheter-based treatments, which are safer and less debilitating.

The second trend is represented by the shift from the use of anti-arrhythmic drugs to minimally invasive catheters or other device-based therapies to palliate incurable arrhythmias. For example, automatic cardioverter-defibrillators are routinely implanted in patients with lethal ventricular arrhythmias to reduce the likelihood of sudden death. Thus, radio frequency (in sub-microwave frequency between 100 kHz to 10 MHz) catheter ablation is now being performed in a large number of patients suffering from cardiac arrhythmias.

Despite these advances in technology, atrial fibrillation ("AF") remains a significant challenge. AF, a rapid irregular rhythm in the atria or upper chambers of the heart induced by non-uniformed electrical pulses, represents a leading cause of stroke and heart attack and a major health care burden. To date, the most effective surgical procedure for the treatment of AF has been the Maze procedure undertaken in "open-heart" surgery. In the Maze procedure, incisions are made along pre-determined lines exterior to the atrium, which are then sutured together. As healing develops, scars are formed along the incision lines thereby forming barriers to the conduction of electrical impulses. By creating such barriers, AF can no longer be sustained and regular heart rhythm is restored. However, the Maze procedure has not been widely adopted due to the morbidity and mortality associated with open-heart surgery, which involves the opening of the chest cavity and cutting of the chest bones.

One new approach to mimic the Maze operation is represented by a catheter-based radio-frequency ablation technique, wherein, instead of surgical incisions, a catheter-electrode is applied to destroy or ablate the heart tissues inside the atrial chamber. The catheter-electrode is passed through the artery for access to the atrium, as commonly practiced in the medical field. Within the atrium, the tip of the catheter-electrode is positioned, usually with the aid of x-ray or fluoroscopic means, and is brought into contact with the heart tissue at a desired location or spot where ablation is required. At this spot, the tissue is destroyed by resistive heating generated from the catheter-electrode. Thereafter, the catheter-electrode is re-positioned to the next spot for ablation. A series of spot ablations thus mimics the lineal lesions as accomplished under the Maze procedure against the conduction of electrical impulses.

Existing catheter-based ablation procedures are recognizably less intrusive than "open-heart" surgery. In addition, during the ablation, disruption of cardiovascular function is reduced. However, a successful catheter-based radio-frequency ablation procedure requires the ablation of tissue spots within the spatial or proximity tolerance between adjacent spots, usually less than 2 millimeters, to prevent the passage of electrical impulses. In that connection, the task for the precise placement of the catheter-electrode represents a critical element of a successful procedure.

A major drawback of such existing procedures is the time-consuming task of positioning the catheter-electrode at the desired ablation spots within the atrium while the heart chamber muscles are pulsating. Movements of the atrial wall or the heart muscles often render accurate placement of the catheter-electrode difficult, and slippage of the catheter-electrode tends to occur thereby damaging portions of the atrium where ablation is not desired. As a result, placement of the catheter based RF ablation cannot be efficiently accomplished, and prolonged procedure time, in excess of 12 hours, can be expected. Further, during the procedure, x-ray or other irradiating means are routinely employed for locating and positioning the catheter-electrode, which dictates the use of heavy lead protective gear by the electro-physiologist. As a result, such inconvenience is often amplified by the prolonged procedure time, which detracts from the use of a catheter-based electrode as an efficient means for tissue ablation.

To address these challenges, for example, in U.S. Pat. No. 5,741,249, a catheter-based microwave antenna is disclosed wherein a distal tip is incorporated into the antenna to anchor it to the atrial wall. However, while this design reduces the likelihood of antenna or catheter-electrode slippage during each ablation step, it does not eliminate the consuming task of securing precise placement of the antenna along the desired ablation path for each ablation step. Thus after each ablation step, the antenna has to be re-positioned and anchored precisely at the next spot which must be located within the spatial or proximity tolerance on the ablation path as referenced above.

Accordingly, effective treatments for atrial fibrillation with catheter ablation will require the creation of long or overlapping lineal or curvilinear ablation lesions on the inner surface of the atrium. These lesions can then act as barriers to the conduction of electrical impulses, thus preventing atrial fibrillation.

It is also recognized that a critical requirement for the effective catheter-based ablation of atrial fibrillation is the ability to stabilize and anchor the catheter and microwave antenna inside the atrial chambers. New catheter ablation systems, preferably capable of producing long or overlapping lineal or curvilinear ablation lesions, are required for the development of minimally invasive catheter-based curative procedures for atrial fibrillation.

U.S. Pat. No. 6,190,382, issued Feb. 20, 2001 and U.S. patent application Ser. No. 09/459,058, filed Dec. 11, 2000, both disclose a radio-frequency or microwave-energy based catheter for ablating biological tissues within the body vessel of a patient. The catheter has a proximal portion, a distal portion with a distal end and a lumen extending from the proximal portion to the distal portion. The catheter incorporates an elongated catheter guide that is located within the catheter lumen and is secured to the distal portion of the catheter at one end, with the other end portion extending proximally within the catheter lumen to be coupled to a positioning mechanism. The catheter guide is deployable beyond the distal end of the catheter to form a loop, which is conformable to the interior contour of the body vessel.

The catheter guide carries the catheter with a radio-frequency or microwave energy based antenna incorporated at the distal portion of the catheter. The antenna includes a helical coil, which accommodates the catheter guide passing through it. The radio-frequency antenna is adapted to receive and irradiate radio-frequency energy in the microwave range at a frequency typically greater than 300 Megahertz (MHz) in the electromagnetic spectrum for ablating biological tissue along a biological ablation pathway.

With further improvements to the above-mentioned radio-frequency or microwave-energy based catheter, U.S. patent application Ser. No. 10/306,757, filed Nov. 27, 2002, which is incorporated by reference as though set forth in full and include the same inventors as the present application, discloses advanced deflectable and shapeable structural features of the catheter and particularly its antenna portion. These features substantially enhance the abilities of the electro-physiologists to adapt the form and shape of the catheter and the antenna to conform with the contour of the ablation site and to accurately prescribe the ablation pathway.

SUMMARY OF THE INVENTION

The catheter of the present invention provides further enhancements and features to the catheter described in U.S. Pat. No. 6,190,382, U.S. patent application Ser. No. 09/459,058 and U.S. patent application Ser. No. 10/306,757.These improvements and features, among others, include a radio-frequency ("RF") generator for selectively generating high frequency RF energy at variable power outputs delivered to the RF antenna. The RF antenna includes a helical coil and has an axial passageway to accommodate the steering control lines.

According to the present invention, an improved radio frequency based catheter system is provided for ablating biological tissues of a body vessel, including the atrium of a patient. The system comprises a RF generator in the microwave frequency range adapted for communicating RF energy to a catheter that is adaptable for insertion into the body vessel and a deflectable antenna guide disposed within the catheter lumen. The catheter comprises an RF transmission line and a deflectable RF antenna provided at the distal portion of the catheter to receive and transmit radio frequency energy for tissue ablation. The antenna includes a helical coil and has an axial passageway to accommodate the antenna guide, which, upon deployment prescribes the ablation pathway of the antenna for tissue ablation. In a representative embodiment of the invention, the antenna guide includes elongated portions that are secured to control slides for positioning and deployment and deflection control. Alignment of the antenna with the desired tissue ablation pathway is facilitated with the use of radio-opaque markers and an antenna element, which is radio-opaque. After the RF antenna is positioned within the body vessel, the RF generator is activated to apply energy to the antenna. The RF generator will monitor and minimize reflected to forward power ratio of the antenna and antenna-tissue interface by adjusting the microwave frequency for efficient tissue ablation.

In a representative embodiment of the invention, the antenna guide includes elongated portions that are secured to control slides for positioning and deployment and deflection control. Alignment of the antenna with the desired tissue ablation pathway is facilitated with the use of radio-opaque markers and/or a radio-opaque antenna element.

After the RF antenna is positioned in the proximity of the body tissue within the body vessel, the RF generator is activated to apply energy to the antenna. The RF generator monitors and minimizes reflected to forward power ratio of the antenna and antenna-tissue interface by adjusting the microwave frequency for efficient tissue ablation.

In one embodiment of the invention, a sensor is deployed to sense the amount of reflected RF energy from the antenna. If the reflected energy is too high, the RF generator will automatically adjust to scale back the frequency of the synthesized waveform in order to maximize energy deliverance to the tissue region.

These and other aspects and advantages of the invention will become apparent from the following detailed description, and the accompanying drawings, which illustrate by way of example the features of the invention.

DETAILED DESCRIPTION

The present invention involves a radio-frequency based catheter system for the ablation of biological tissues, as shown in FIG. 1. In particular the present invention is adaptable to ablate tissues located in the internal vessels of living mammals by way of a radio-frequency (RF) antenna that is incorporated as part of a catheter. The catheter is insertable within the internal lumens or body vessels of such mammals and the RF antenna is placed in proximity of the tissues to be ablated where RF energy is applied to effect the tissue ablation.

The invention provides a means for generating a train of RF energy pulses, especially in the microwave frequency range, which are delivered via an electrical transmission line to the RF antenna. The frequency of the RF energy pulses can be selectively varied according to the electrical characteristics of the electrical transmission line and the load impedance associated with the tissue ablation.

The invention also incorporates a means for sensing the forward and the reflected powers associated with the microwave frequency energy pulses, on which a reflected-to-forward power ratio is defined. Adjusting the output frequency of the energy pulses of the RF generator to minimize the reflected-to-forward power ratio, the present invention fine-tunes the impedance of the system energy output to substantially match that of the ablation load and delivers the ablation energy to where it is needed. Thus, the present invention provides not only the means for generating and delivering RF energy to the RF antenna for tissue ablation, but also a means to maximize the operational efficiency of the RF antenna, which reduces the risks of overheating the electrical transmission line.

Figure 1A:
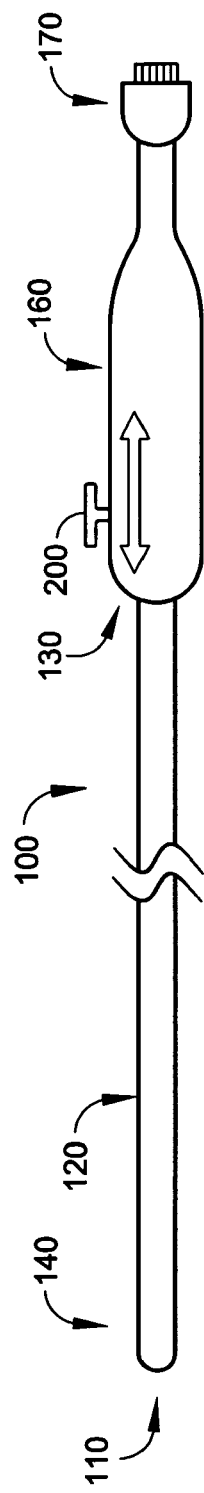
FIG. 1 is a representative Radio-Frequency based catheter of the present invention.
Figure 1B:
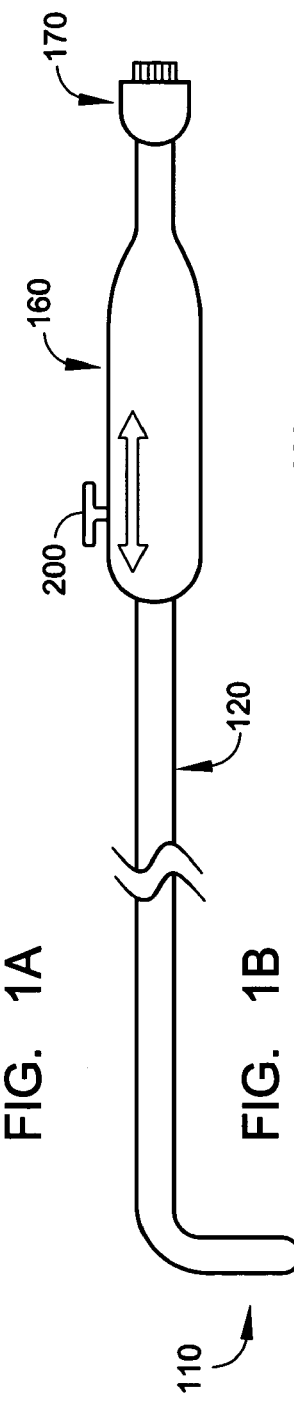

With reference to FIGS. 1A and 1B, a radio-frequency ("RF") ablation catheter 100 including a shapeable antenna apparatus 110 constructed in accordance with an embodiment of the present invention is shown. The catheter 100 is adaptable for insertion into a body vessel of patient and the shapeable antenna apparatus 110 includes a radio-frequency antenna for delivering electromagnetic energy to a treatment site. The catheter 100 will first be described before describing the shapeable antenna apparatus 110 of the present invention.

The catheter 100 has a flexible elongated tubular body 120 with a proximal portion 130 and a distal portion 140. One or more intracavity lumens 150 (FIGS. 3A, 3B) extend from the proximal portion 130 of the catheter 100 to the distal portion 140. Located at the proximal portion 130 of the catheter 100 is a handle chassis 160 for housing necessary steering and positioning controls, as will be described in further detail below. Incorporated at a proximal end 160 of the catheter 100 is a coupling 170 for connecting the catheter 100 to one or more electronic devices such as an RF generator and controller (not shown) in support of the ablation procedure.

The dimensions of catheter 100 are adapted as required to suit the particular medical procedure, which are well known in the medical art. In a preferred embodiment, the catheter 100 is used to ablate cardiac tissue; however, the catheter 100 may be used to ablate other types of body tissue. The tubular body 120 of the catheter may be generally constructed of a polymer material that is bio-compatible within the body vessel environment. Examples of these materials include, but not by way of limitation, Pebax from Autochem Germany, polyethylene, polyurethane, polyester, polyimide and polyamide, with varying degrees of radiopacity, hardness and elasticity.

The catheter 100 may be formed with a plurality of segments using one or more of the aforementioned materials such that the catheter body 120 is progressively more flexible toward its distal end. The segments may be joined together by thermal bonding, butt joint, or adhesive bonding. Braiding reinforcement can also be added to the circumferential surface of tubular body 120 to attain the desirable level of stiffness and torsional strength for the catheter 100. This allows the catheter 100 to advance and negotiate through the body vessel of a patient, and to enable torque transfer along the length of the catheter from the proximal portion to the distal portion.

Figure 3:
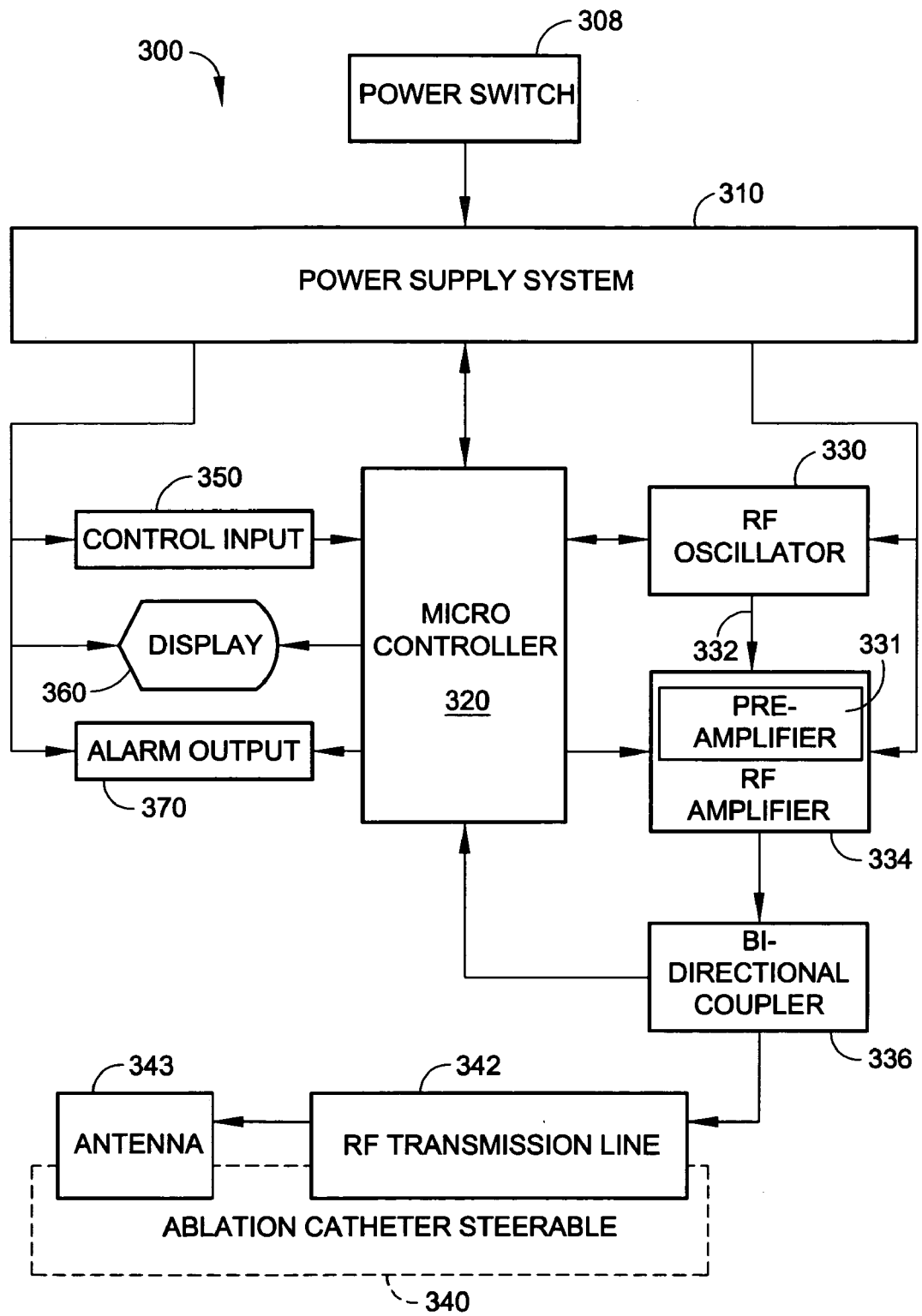
FIG. 3 is a schematic block diagram of a radio frequency based catheter system according to an embodiment of the invention.
Figure 3A:
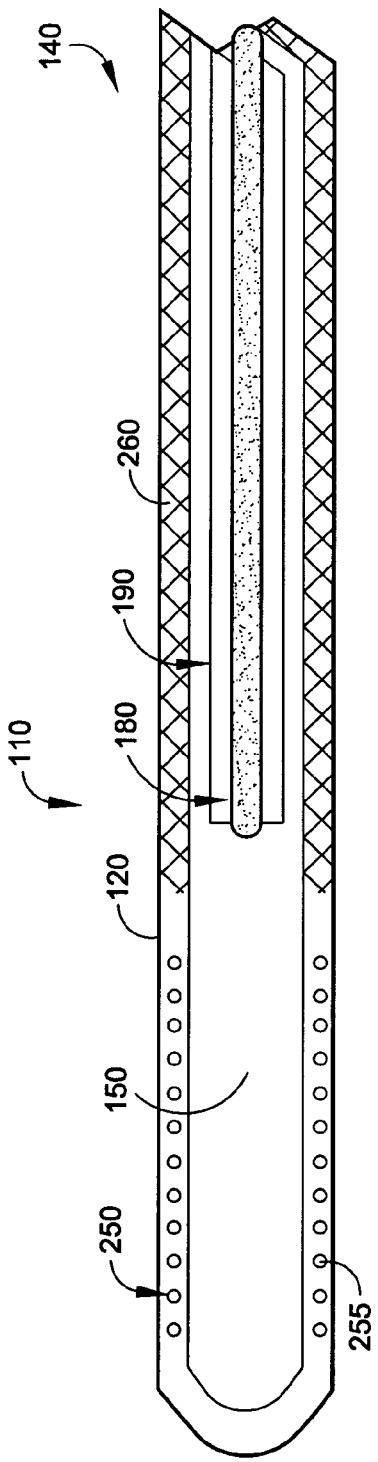
Figure 3B:
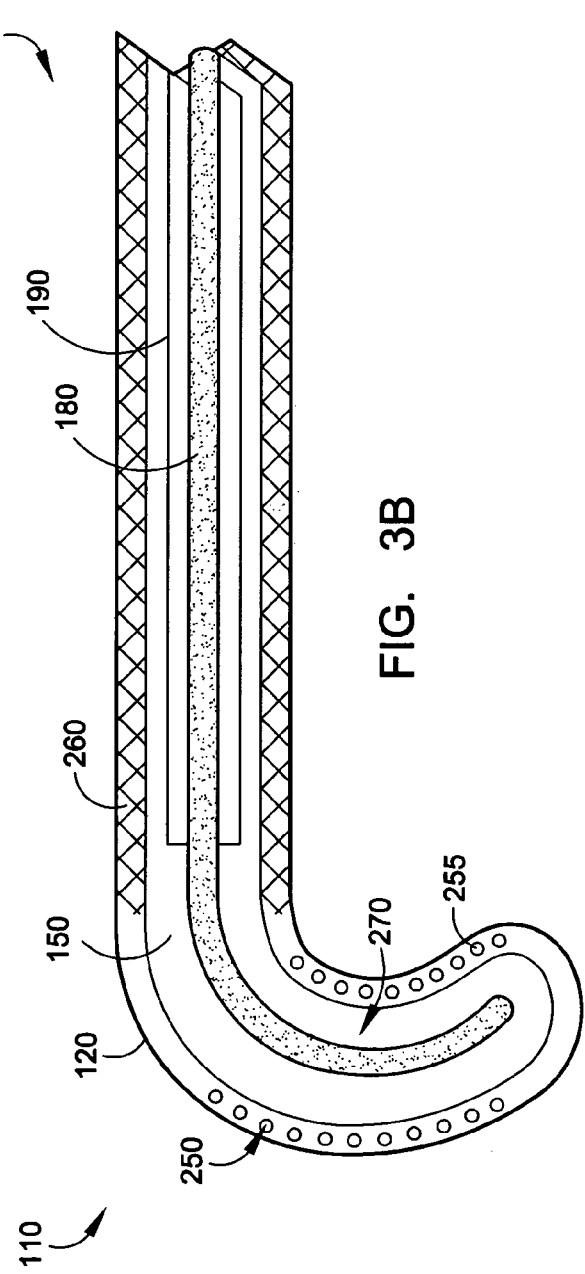

With reference additionally to FIGS. 3A and 3B, the distal portion 140 of catheter body 120 may include a softer polymer compound than the proximal portion 130, with little or no braiding, to provide the desired flexibility to accommodate distal deflection and shaping of the shapeable antenna apparatus 110. Deflection and shaping of the shapeable antenna apparatus 110 may be implemented through the use of a pre-shaped deflection member 180 and a deflection regulating member 190. The pre-shaped deflection member 180 and/or the deflection regulating member 190 may extend from the handle chassis 160 to the distal portion 140 of the catheter body 140.

The pre-shaped deflection member 180 and/or the deflection regulating member 190 may be proximally fastened to deflection control mechanism 220 or thumb slide 200 (FIGS. 1A, 1B), which may be slidably engaged along a axial slot of the handle chassis 160. Axial movement of the thumb slide 200 along the axial slot, together enables a physician to shape or deflect the shapeable antenna apparatus 110 between a straight configuration (FIG. 1A) and a deflected, shaped configuration (FIG. 1B), or any configuration therebetween. A frictional capture mechanism (not shown) may be incorporated in the thumb slide 200 to maintain the grip position in the axial slot. Many such means are commercially available. Examples of such means include set-release, pressure switch or self-locking mechanisms.

Figure 2A:
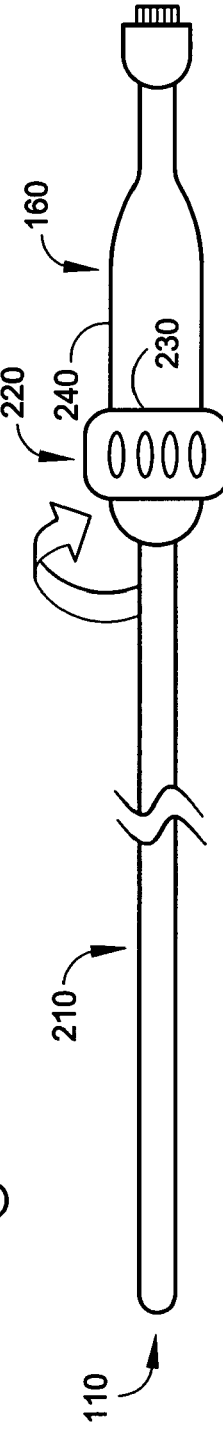
FIG. 2 is a representative Radio-Frequency based catheter of the present invention.
Figure 2B:
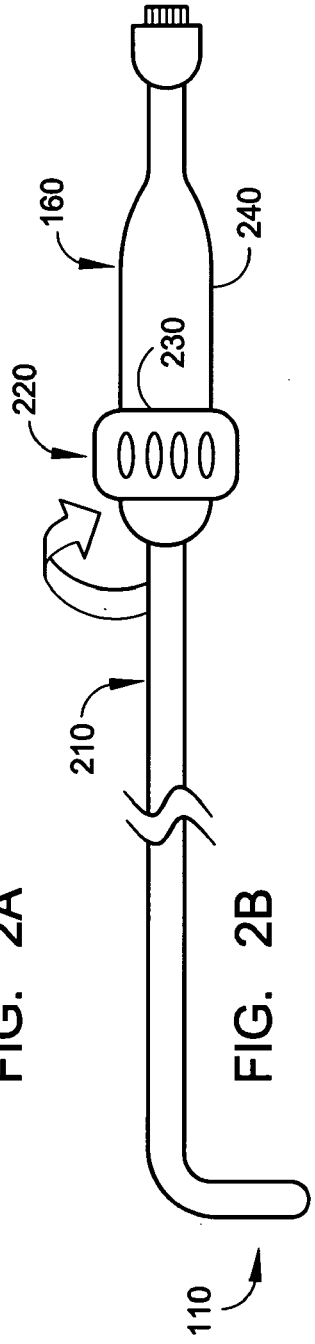

FIGS. 2A and 2B illustrate an RF ablation catheter 210 similar to the RF ablation catheter 100 described above, but with an alternative embodiment of a deflection control mechanism 220 for shaping or deflecting the shapeable antenna apparatus 110. The deflection control mechanism 220 may include a rotatable collar 230 that circumferentially surrounds and is rotatably coupled to a handle shaft 240 of the handle chassis 160 to control axial movement of the pre-shaped deflection member 180 and/or the deflection regulating member 190. The handle chassis 160 may house a translation mechanism that translates rotation movement of the collar 230 to axial movement of the pre-shaped deflection member 180 and/or the deflection regulating member 190. Rotational movement of the collar 230 relative to the handle shaft 240 enables a physician to shape or deflect the shapeable antenna apparatus 110 between a straight configuration (FIG. 2A) and a deflected, shaped configuration (FIG. 2B), or any configuration therebetween.

FIG. 3 is a schematic block diagram of a radio frequency based catheter system according to an embodiment of the invention, illustrating the electrical and signal components of the system. Catheter system 300 has a power switch 300, power supply system 310, micro-controller system 320, RF signal generator or oscillator 330, RF amplifier 334 comprising a pre-amplifier 331, RF bidirectional coupler 336, ablation catheter 340, control input 350, display 360, and alarm output 370. The ablation catheter 340 includes a catheter steering and deflection mechanism (not shown), RF transmission line 342, and RF antenna 343.

The RF based catheter system 300 is powered by ordinary alternating current power and it could be adapted to be powered by an appropriate direct current source as well. The power switch 300 connects the electrical power to the system power supply 310. The system power supply provides primary patient safety isolation and synthesizes various direct current voltages necessary to operate the apparatus to effect tissue ablation.

The microcontroller 320, which is microprocessor based, provides for user input, displays for inputs and outputs, and sets system alarm conditions. Microcontroller 320 also monitors and controls RF power synthesis and communication to the RF antenna 343 and ablation tissue. As shown in FIG. 3, the microcontroller 320 monitors and controls RF signal oscillator 330, which receives power from the power supply system 310. RF signal oscillator generates a continuous RF frequency wave signal 332 at a power level and frequency determined and controlled by micro controller 320.

In the embodiment of the present invention, the RF signal oscillator 330 is electrically coupled to the power amplifier 334. The power amplifier 334 includes a preamplifier 331, which initially amplifies the wave signal 332 from the RF generator and produces a first train of relatively low energy pulses. After amplification by RF amplifier 334, the energy pulses are then delivered via a transmission line 342 to an RF antenna 343, which as been placed in the proximity of the tissue to be ablated.

As shown in FIG. 2, the bidirectional coupler 336 is electrically interposed between the amplifier 334 and transmission line 342. The coupler samples the relatively low energy forward pulses along the transmission line and the energy pulses reflected from the target ablation tissue and uses the signal samples as feedback to the micro controller 320. The feedback mechanism provided by sampling the signal at the coupler 336 is useful for scaling back the amount of reflected energy. Too much signal reflection could potentially destroy sensitive system 300 components or cause patient injury.

Electrically in communication with the bi-directional coupler 336, the micro-controller 320 monitors the forward and reflected energy pulses. Micro-controller 320 then defines a ratio for the reflected and forward energy pulses. In one embodiment, this ratio comprises a voltage standing wave ratio (VSWR), computed as:

$$VSWR = \frac{1 + |\Gamma_0|}{1 - |\Gamma_0|}$$

Where $\Gamma_0$ represents the load reflection coefficient computed using the appropriate boundary conditions along RF transmission line 342.

A low ratio would indicate that most of the energy generated by the system is applied to the load for ablation, and is characteristic of having achieved matched impedance between the apparatus and the ablation load. A high ratio, on the other hand, would indicate that a significant amount of the energy generated by the system is being reflected, and is characteristic of a high degree of return loss, or leakage, resulting from a poor impedance match.

To the extent that the impedance of RF transmission line 342 is affected by the pulse 332 frequency, the present invention provides a means to enable the change of frequency in the power output of the system such that both the line impedance and the load impedance will be matched. The means for sensing (i.e., the bidirectional coupler, in one embodiment) and the means for adjusting comprise a means for adjusting RF signal source 330 and RF power amplifier 334 in response to the means for controlling (i.e., the micro controller 320) to match the transmission line impedance to the load impedance. For example, if the ratio indicates that too much energy is being reflected (e.g., VSWR is high), the micro controller 320 adjusts the frequency of the RF signal 332 generated by the oscillator 330 to effect a reduced value in the ratio of the reflected and forward energy pulses. Such a reduction in the power ratio effects impedance matching between the transmission line and the ablation load. An acceptable amount of return loss would depend upon the application. However, since a perfect impedance match is never achievable, micro controller 320 can allow for the user to adjust the frequency such that the ratio drops below some threshold value, such as 1.4:1.

Because load impedance can vary widely among tissue types and can vary according to the quality and quantity of fluids surrounding the tissue, such as in a blood-filled cavity or chamber, the means for controlling supports a broad range of frequency adjustment settings to enable flexible deployment of system 300 in the field.

Having achieved a match in the impedance, the inventive apparatus adjusts the power amplifier 334 to produce the train of relatively high energy pulses, which will be delivered via the transmission line to the RF antenna to effect tissue ablation. In one example of the present invention, the power lever generated for ablation process was approximately 60 watts.

In addition to providing monitoring and adjusting functions over the frequency of the RF pulses, the microcontroller 320 also communicates the various signals and indicators to a user such as electro-physiologist. The system supports manual override in the RF frequency, output power, and setting the ablation duration. In a typical configuration, the control input 350 of the present invention may be equipped with a multi-line display, a set of up and down keys for adjusting output power level and ablation period, a ablation on/off key for activating ablation processes, and a mode/setup key for changing display mode and/or configuring an I/O port.

The output power level of the RF amplifier 334 is monitored continuously during ablation processes. The RF bi-directional coupler 336 provides the ability to sample both forward and reverse power levels at attenuated levels that are electrically connected to the micro-controller assembly. The micro-controller assembly compares the two signals and adjusts both the signal source and the preamplifier/power amplifier gains to achieve lowest reverse-to-forward power ratio.

The RF based catheter system 300 monitors and controls the microwave frequency and power output within typical range of 900 MHz to 930 MHz to minimize reflected-to-forward power ratio. The RF antenna 343 is typically manufactured and tuned to 915 MHz in the saline solution closely approximating biological tissue and fluid filled animal body vessel to be ablated. Upon entering the body vessel and coming in contact with the biological tissue to ablation, the electrical dimension of the RF antenna 343 may slightly altered temporary to cause reflected power to increase. Increased reflected power reduces overall power available for irradiation and therefore, reduces efficient tissue ablation. If the reflected power is left unchecked and increases greatly, local heating of the RF antenna 343 may occur and produce unwanted ablation affects.

Figure 4:
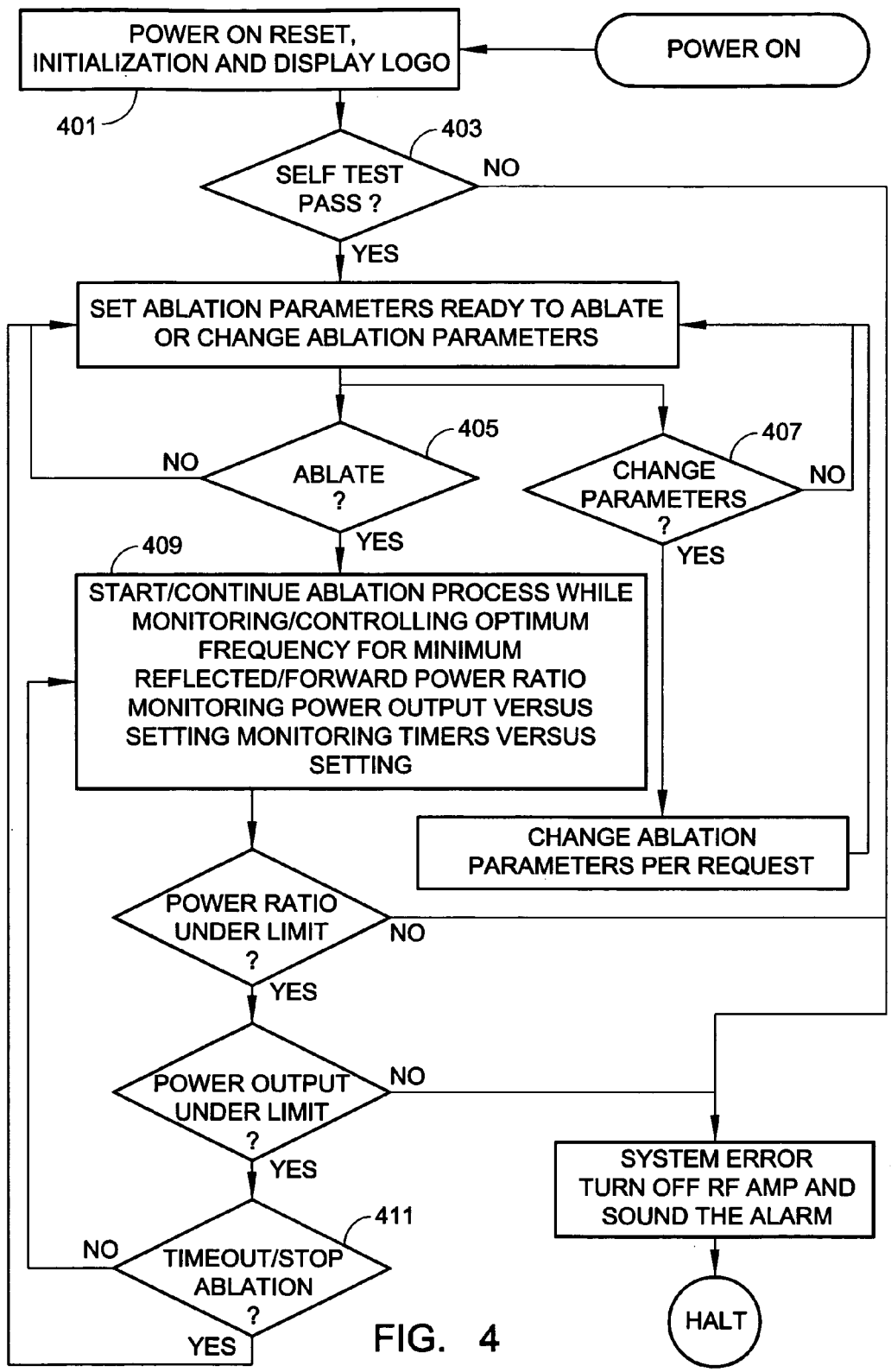
FIG. 4 is a flow diagram illustrating a method of establishing and controlling microwave frequency to minimize reflected to forward power ratio of an apparatus according to an embodiment of the invention.

FIG. 4 is a flow diagram of a method for biological tissue ablation according to an embodiment of the invention. Such a method can be used to program the instruction set of microcontroller 320 in order to carry out the ablation procedures described herein.

The process begins after the system is powered on by a user, usually by engaging power switch 301. In step 401, the system normally runs a battery of initialization routines in order to establish system integrity. Self-test can comprise, for example, displaying a logo on a display and checking system ROM for appropriate hardware.

In condition block 403, the process branches to a system error if the power-on self test fails. In one embodiment, if the self-test failed on power-on, then an alarm will sound.

If the self-test passes in condition block 403, then ablation parameters can be set either automatically, or manually by the electro-physiologist in step 405

In condition block 405, if ablation has not been successful after a period of applying RF energy to the region of interest, then a control signal can be sent back to the user or to microcontroller 320 permitting the appropriate ablation parameter adjustment (step 407).

In step 409, ablation continues under constant monitoring conditions, so that an appropriate adjustment can be made to the frequency of oscillator 330, such as in the case that the measure of reflected-to-forward power is too high. Several parameters can be monitored in real-time to insure that critical system thresholds are not exceeded. For example, power output in step 411 can be monitored as well to insure that the prescribed amount of ablation exposure is provided.

Too much exposure, and unwanted results, such as ablation of surrounding benign tissue, could result.

The radio-frequency based catheter system and method for ablating biological tissues can be adapted to a variety of medical uses. The description and drawings contained herein represent the presently preferred embodiment of the invention and are, as such, a representative of the subject matter which is broadly contemplated by the invention. The scope of the invention fully encompasses other embodiments that may become obvious to those skilled in the art, and the scope of the present invention is accordingly limited by nothing other than the appended claims.

What is claimed is:

1. A method for biological tissue ablation, comprising:
   shaping a shapeable RF antenna to accommodate the contour of a body vessel adjacent a biological tissue load;
   generating a train of radio frequency (RF) energy pulses at an output frequency for transmission in a transmission line to the shapeable RF antenna deployable adjacent to the biological tissue load;
   sensing a reflected signal and a forward signal of the RF energy pulses;
   determining a voltage standing wave ratio (VSWR) based on the reflected signal and the forward signal; and
   adjusting the output frequency of the RF energy pulses based on the VSWR to effect a substantial match of transmission line impedance with shapeable RF antenna and biological tissue load impedance.

2. The method of claim 1, wherein the substantial match of the transmission line impedance with the load impedance is characterized by minimum signal reflection.

3. The method of claim 2, wherein minimum signal reflection is characterized by a measurement of the voltage standing wave ratio (VSWR).

4. The method of claim 3, wherein the output frequency is adjusted such that the VSWR is below a preset threshold value.

5. The method of claim 1, further comprising amplifying the train of radio frequency (RF) energy pulses.

6. The method of claim 1, further comprising sampling the forward signal and the reflected signal using a bi-directional coupler.

7. The method of claim 1, further comprising using a catheter to deploy the RF antenna to the biological tissue load.

8. The method of claim 1, further comprising accepting user inputs from a user.

9. The method of claim 1, further comprising setting alarm conditions and outputting alarms to a user.

10. The method of claim 1, further comprising displaying inputs and outputs on a display.

11. A system for biological tissue ablation comprising:
    shapeable RF antenna means for accommodating the contour of a body vessel adjacent a biological tissue load;
    means for generating a train of radio frequency (RF) energy pulses at an output frequency for transmission in a transmission line to the shapeable RF antenna means deployable adjacent to the biological tissue load;
    means for sensing a reflected signal and a forward signal of the RF energy pulses when the shapeable RF antenna means is adjacent to the biological tissue to be ablated;
    means for determining a voltage standing wave ratio (VSWR) based on the reflected signal and the forward signal; and
    means for adjusting the output frequency of the RF energy pulses based on the VSWR to effect a substantial match of a transmission line impedance with shapeable RF antenna and biological tissue load impedance.

12. The system of claim 11, wherein the substantial match of the transmission line impedance with the load impedance is characterized by minimum signal reflection.

13. The system of claim 12, wherein minimum signal reflection is characterized by a measurement of the voltage standing wave ratio (VSWR).

14. The system of claim 13, wherein the output frequency is adjusted such that the VSWR is below a preset threshold value.

15. The system of claim 11, further comprising means for amplifying the train of radio frequency (RF) energy pulses.

16. The system of claim 11, further comprising means for sampling the forward signal and the reflected signal.

17. The system of claim 11, further comprising means for deploying the RF antenna to the biological tissue load.

18. The system of claim 11, further comprising means for accepting user inputs from a user.

19. The system of claim 11, further comprising means for setting alarm conditions and means for outputting alarms to a user.

20. The system of claim 11, further comprising means for displaying inputs and outputs.

21. A system for biological tissue ablation comprising:
    a shapeable RF antenna to accommodate the contour of a body vessel adjacent a biological tissue load;
    an oscillator for generating a train of radio frequency (RF) energy pulses at an output frequency for transmission in a transmission line to the shapeable RF antenna deployable adjacent to the biological tissue load;
    a bi-directional coupler for sensing a reflected signal and a forward signal of the RF energy pulses when the shapeable RF antenna is adjacent to the biological tissue to be ablated; and
    a microcontroller for determining a voltage standing wave ratio (VSWR) based on the reflected signal and the forward signal, and for adjusting the output frequency of the RF energy pulses based on the VSWR to effect a substantial match of a transmission line impedance with shapeable RF antenna and biological tissue load impedance.

22. The system of claim 21, further comprising a power amplifier for amplifying the train of RF energy pulses.

23. The system of claim 21, further comprising a pre-amplifier for pre-amplifying the RF frequency pulses prior to being amplified by the power amplifier.

24. The system of claim 21, further comprising a display coupled to the microcontroller.

25. The system of claim 21, further comprising an input control coupled to the microcontroller.

26. The system of claim 21, further comprising an alarm output coupled to the microcontroller.

27. The system of claim 21, wherein the RF antenna is deflectable.

28. The system of claim 21, further comprising a catheter to deploy the RF antenna to the biological tissue load.

* * * * *